(12) United States Patent
Zweymuller

(10) Patent No.: US 7,455,693 B2
(45) Date of Patent: *Nov. 25, 2008

(54) LEAFLIKE SHAFT OF A HIP-JOINT PROSTHESIS FOR ANCHORING IN THE FEMUR

(75) Inventor: Karl Zweymuller, Vienna (AT)

(73) Assignee: Smith & Nephew Orthopaedics, AG, Rotkreuz (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/432,914

(22) Filed: May 12, 2006

(65) Prior Publication Data

US 2006/0206212 A1    Sep. 14, 2006

Related U.S. Application Data

(60) Continuation of application No. 10/355,385, filed on Jan. 30, 2003, now Pat. No. 7,175,668, which is a division of application No. 09/548,166, filed on Apr. 13, 2000, now Pat. No. 6,540,788.

(30) Foreign Application Priority Data

Apr. 13, 1999   (DE)   ................. 199 16 629
Jun. 23, 1999   (DE)   ................. 199 28 791

(51) Int. Cl.
A61F 2/32   (2006.01)
A61F 2/36   (2006.01)

(52) U.S. Cl. ............... 623/22.12; 623/23.26; 623/23.35

(58) Field of Classification Search .............. 623/22.12, 623/23.15–23.47
See application file for complete search history.

(56) References Cited

U.S. PATENT DOCUMENTS

| | | | |
|---|---|---|---|
| 3,064,645 A | 11/1962 | Ficat et al. | |
| 3,067,740 A | 12/1962 | Haboush | |
| 4,199,824 A | 4/1980 | Niederer | |
| 4,359,785 A | 11/1982 | Niederer | |

(Continued)

FOREIGN PATENT DOCUMENTS

AT    391 264 B    9/1990

(Continued)

OTHER PUBLICATIONS

Bohm, G., Lintner, F., Auterith, A., Lester D.K., Zweymuller, K., *Morphometric Examination of Straight, Tapered Titanium Stems*, Clinical Orthopaedics and Related Research, 2001, pp. 13-24, No. 393, Lippincott Williams & Wilkins, Inc.

(Continued)

*Primary Examiner*—Bruce E. Snow
(74) *Attorney, Agent, or Firm*—Knobbe, Martens, Olson & Bear, LLP

(57) ABSTRACT

Leaflike shaft (1) of a hip-joint prosthesis for anchoring in the femur, according to a towards a distal end (5), with a femur-anchoring section (1a, ... 1i) having a long axis (A) and with a prosthesis neck (2), wherein the femur-anchoring section (1a, ... 1i) has a substantially rectangular external contour in a plane perpendicular to the long axis (A), optionally with recesses in the side edges and/or at the corners.

15 Claims, 5 Drawing Sheets

U.S. PATENT DOCUMENTS

| | | | |
|---|---|---|---|
| 4,404,693 | A | 9/1983 | Zweymuller |
| 4,661,112 | A | 4/1987 | Mueller |
| 4,664,668 | A | 5/1987 | Beck et al. |
| 4,728,334 | A | 3/1988 | Sportorno |
| 4,813,962 | A | 3/1989 | Deckner et al. |
| 4,865,608 | A | 9/1989 | Brooker, Jr. |
| 4,904,262 | A | 2/1990 | Brensmann |
| 4,908,035 | A | 3/1990 | Deckner et al. |
| 4,979,958 | A | 12/1990 | Niwa et al. |
| 5,133,770 | A | 7/1992 | Zweymuller et al. |
| 5,152,799 | A | 10/1992 | Lyons |
| 5,456,717 | A | 10/1995 | Zweymuller |
| 5,480,452 | A | 1/1996 | Hofmann et al. |
| 5,507,833 | A | 4/1996 | Bohn |
| 5,593,451 | A | 1/1997 | Averill et al. |
| 5,593,452 | A | 1/1997 | Higham et al. |
| 5,665,090 | A * | 9/1997 | Rockwood et al. ............ 606/80 |
| 5,725,586 | A | 3/1998 | Sommerich |
| 5,725,595 | A | 3/1998 | Gustilo |
| 5,755,811 | A | 5/1998 | Tanamal et al. |
| 5,928,289 | A | 7/1999 | Deckner |
| 6,190,417 | B1 | 2/2001 | Itoman et al. |
| 6,224,634 | B1 | 5/2001 | Keller |
| 6,245,111 | B1 | 6/2001 | Shaffner |
| 6,436,148 | B1 | 8/2002 | DeCarlo et al. |
| 6,540,788 | B1 | 4/2003 | Zweymuller |
| 6,808,539 | B2 | 10/2004 | Zweymuller |
| 7,175,668 | B2 | 2/2007 | Zweymuller |

FOREIGN PATENT DOCUMENTS

| | | |
|---|---|---|
| DE | 23 24 865 | 5/1973 |
| DE | 26 27 569 A1 | 12/1977 |
| DE | 87 12607.9 | 9/1987 |
| DE | 38 19 948 | 6/1988 |
| DE | 2805 305 C2 | 3/1989 |
| DE | 90 06 893.9 | 6/1990 |
| DE | 41 29 724 A1 | 3/1993 |
| DE | 43 15 143 | 5/1993 |
| DE | 42 23 373 A1 | 1/1994 |
| DE | 94 02 934.2 | 10/1994 |
| DE | 295 06 036.0 | 4/1995 |
| DE | 297 05 500 U1 | 9/1998 |
| EP | 0 159 510 A2 | 10/1985 |
| EP | 0 159 510 A3 | 3/1987 |
| EP | 0 289 922 | 1/1988 |
| EP | 0 159 510 B1 | 5/1990 |
| EP | 0 720 839 A1 | 12/1995 |
| EP | 0 700 670 A1 | 3/1996 |
| EP | 0 821 923 | 7/1997 |
| EP | 1 044 665 A3 | 1/2001 |
| FR | 2 315 902 | 1/1977 |
| FR | 2 639 821 A1 | 12/1988 |
| FR | 2 634 642 | 2/1990 |
| FR | 2 681 239 | 9/1991 |
| FR | 2 699 398 | 12/1992 |
| WO | WO 00/59410 | 10/2000 |

OTHER PUBLICATIONS

Clements, J.P., Gheduzzi, S., Zweymuller, K., Lintner F., Schmotzer, H. Learmonth, I.D., Miles, A.W., *An In Vitro Cadaveric Biomechanical Evaluation of a Cementless Hip stem Comparison of Long and Short Term Stability*, 51st Annual Meeting of the Orthopaedic Research Society, 2005, Paper No. 0266, Centre for Orthopaedic Biomechanics, University of Bath, UK.

Osteonics Brochure for Omniflex-Ha™ Total Hip System, 1991, 8 pages.

Depuy, Inc. Brochure for the AML™ Femoral Component with Porocoat®, 1983, 2 pages.

Operating Technique Manual for the AML™ Total Hip System, available before Apr. 9, 2002, 32 pages.

Slide Presentation with Hip Stem Designs Available Before Apr. 9, 2002, 2 pages.

* cited by examiner

LEAFLIKE SHAFT OF A HIP-JOINT PROSTHESIS FOR ANCHORING IN THE FEMUR

CROSS-REFERENCE TO RELATED APPLICATIONS

This application is a continuation application of U.S. patent application Ser. No. 10/355,385, filed on Jan. 30, 2003, now U.S. Pat. No. 7,175,668, which is a divisional of U.S. patent application Ser. No. 09/548,166, filed on Apr. 13, 2000, now U.S. Pat. No. 6,540,788.

BACKGROUND OF THE INVENTION

1. Field of the Invention

The invention relates to a leaf-like shaft of a hip-joint prosthesis for anchoring in the femur, with a femur-anchoring section and a prosthesis neck.

2. Description of the Related Art

Profiled shafts of this kind are generally known. As only a few examples in this regard reference is made to the patents EP 0 427 902 B1 or EP 0 244 610 B1 or U.S. Pat. No. 4,908,035.

As a rule the anchoring section of a shaft of the kind in question here is constructed with smooth surfaces. In EP 0 427 902 B1 it is proposed to construct one section of the shaft with contact surfaces provided with saw teeth. This measure is intended to improve fusion of the shaft to the bony substance.

It is disclosed in the patent CH-A 642 252 that the anterior and posterior leaf surfaces of the leaf part of a shaft are provided with groove-like indentations. However, bone tissue grows poorly into these. The tissue that fills up these indentations is generally a connective tissue with only slight stability.

SUMMARY OF CERTAIN INVENTIVE ASPECTS

The object of the present invention is to configure the femur-anchoring section of a leaflike shaft in such a way that the tissue growing onto the prosthesis consists to the greatest possible extent of spongy bone tissue, so as to ensure long-term, firm retention of the shaft in the femur.

This object is achieved by a leaf-like shaft with a femur-anchoring section that has an external contour in a plane perpendicular to the long axis that is substantially rectangular, and optionally includes recesses in the sides and/or at the corners and/or in the interior of the shaft.

The invention includes the fundamental idea that the femur-anchoring section of the shaft is substantially rectangular in cross section, so that in simplified (ignoring the tapering toward the tip) terms it is constructed as a "four-edged" profile, in particular as:

Oblique-cross profile;
H profile;
Double-H or -comb profile;
Rectangular hollow profile;
Rectangular facet profile;
Rectangular notch profile;
Approximately trapezoidal profile (with or without recesses at the sides or in the interior)
Or the like.

These profiles all exhibit, to a greater or lesser extent, the property that in the space between the anchoring section of the shaft and the wall of the surgically created cavity spongy bone tissue forms, so that revascularization of the bone occurs. The alternatives in accordance with the invention have the advantage that their periphery comprises substantially four edges, situated at the corners of a rectangle or trapezoid that extends perpendicular to the central axis of the shaft. This basic shape of the shaft has been found in practice to be particularly advantageous for the revascularization of the bone tissue.

It has further been found that a predetermined over-dimensioning of the side surfaces of the shaft in comparison to the "rasped" dimension ("null dimension")—with the exception of the edge regions, which should fit precisely—is advantageous in this respect, especially in the proximal section of the shaft.

With the further development in accordance with the invention the revascularization of the bone tissue is additionally promoted, while on one hand the necessary stability or solidity of the shaft is preserved, but on the other hand the intervening space between shaft and operation-cavity wall is enlarged, with the result that a greater amount of new spongiosa is formed.

BRIEF DESCRIPTION OF THE DRAWINGS

Advantageous details of the prosthesis shaft in accordance with the invention are presented in the subordinate claims and explained in detail in the following description of exemplary embodiments with reference to the attached drawings, wherein

DETAILED DESCRIPTION OF CERTAIN INVENTIVE EMBODIMENTS

Figure 1:
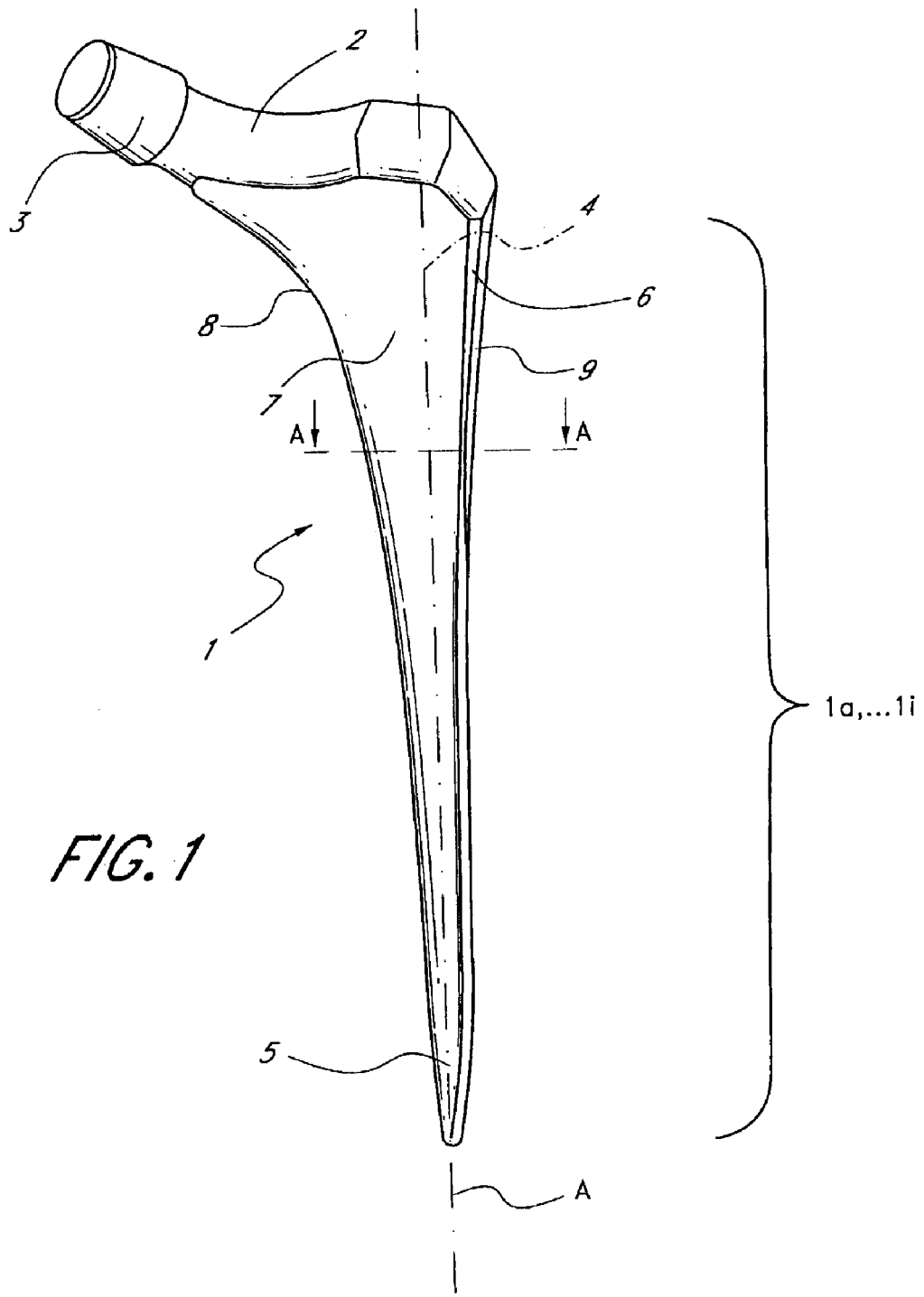
FIG. 1 is a perspective view of a leaf-like shaft, the femur-anchoring section of which is further developed in accordance with the invention.

FIG. 1 shows, in perspective, a leaf-like shaft 1 of a hip-joint prosthesis for anchoring in the femur. The exemplary embodiment shown here comprises an anchoring section $1a, \ldots 1i$ (see FIGS. 2 to 10), which expands conically on all sides from a distal end 5 to the proximal region, where on the medial side it merges with a continuously curving arch 8. This arch 8 is continuous with a prosthesis neck 2, onto which is set a conically tapering peg 3 which receives a spherical joint head. The prosthesis neck axis intersects the central long axis (not shown in FIG. 1) of the shaft and the anchoring section $1a \ldots 1a$ at an angle that corresponds substantially to the angle between the neck and axis of the femur in a natural hip joint.

Laterally in the proximal region of the shaft 1 a trochanter wing 4 is formed, which is laterally delimited by a side surface 9. The transition between the lateral surface and the posterior or anterior surface is defined by a slanted edge 6 that extends from distal to proximal in the region of the trochanter wing 4. The "leaf" of the shaft 1 is defined in the proximal region and is identified by the reference numeral 7.

In FIGS. 2-10 various cross sections or profile shapes of anchoring sections $1a \ldots 1i$ of the shaft 1 are shown.

Figure 2:
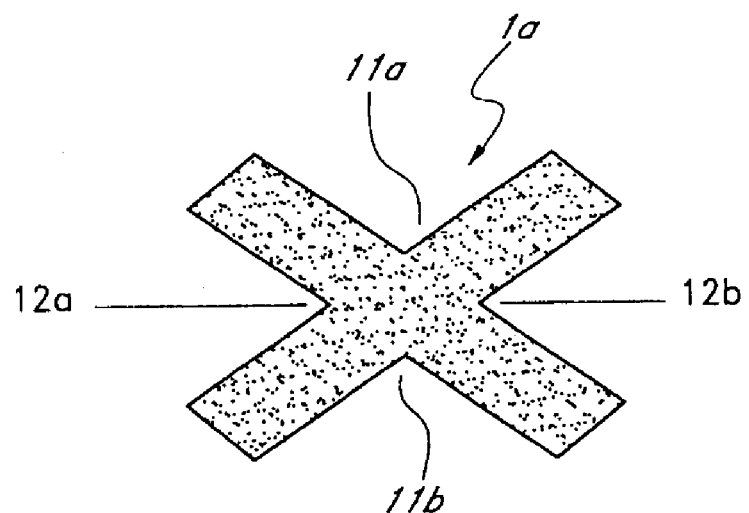
FIGS. 2-9 show various cross sections of the anchoring section of the shaft according to FIG. 1 along the line A-A in FIG. 1.

According to FIG. 2, the anchoring section $1a$ is constructed as an oblique-cross profile, the limbs of which form V-shaped grooves $11a$, $11b$ on the anterior and posterior aspects respectively, each of which has an angle greater than 90°, and laterally and medially form V-shaped grooves 12a, 12b with an angle smaller than 90°.

Figure 3:
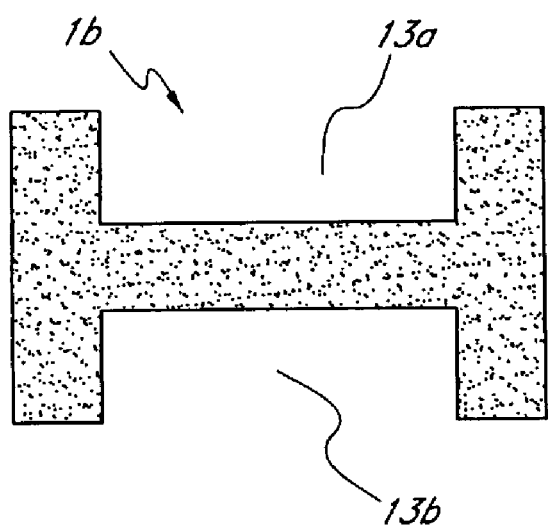

In the embodiment according to FIG. 3 the anchoring section 1b of the shaft 1 is constructed as an H profile. This profile comprises rectangular recesses 13a, 13b on the posterior and the anterior aspect.

Figure 4:
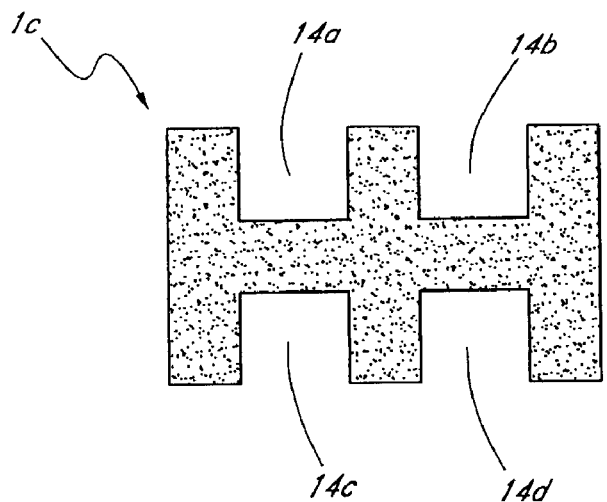

FIG. 4 shows another variant, in which the anchoring section 1c of the shaft 1 is a double-H profile or double-comb profile, in that rectangular longitudinal grooves 14a, 14b, 14c, 14d are formed on the posterior and anterior aspects of the anchoring section.

Figure 5:
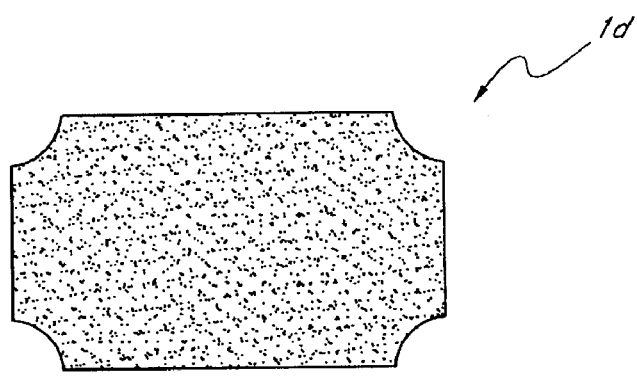

In the variant shown in FIG. 5, the anchoring section 1d of the shaft 1 is roughly rectangular in cross section, with concave facets formed at the four corners. In the illustrated embodiment, each of the facets between adjacent surfaces extends along a circular arc from one of the surfaces to one of the adjacent surfaces. Each facet preferably defines a quarter-circle between any two adjacent surfaces.

Figure 6:
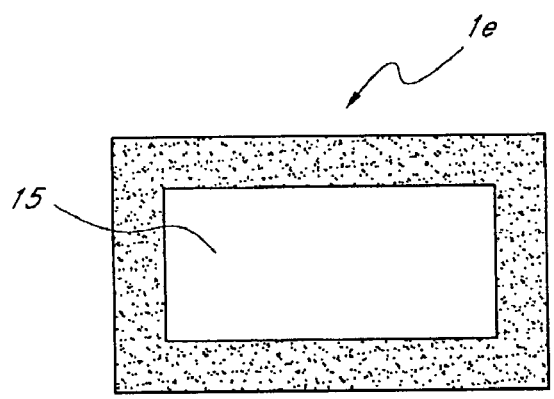
Figure 7:
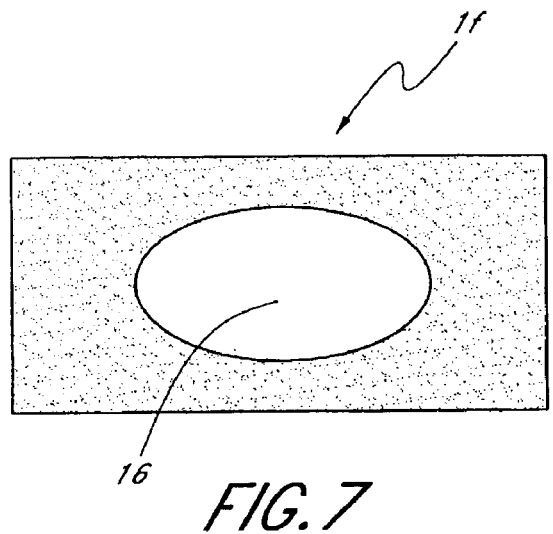

The embodiments according to FIGS. 6 and 7 comprise an anchoring section 1e and 1f, respectively, in the form of a rectangular hollow profile, the embodiment according to FIG. 6 having a cavity 15 that is rectangular in cross section, whereas in the embodiment according to FIG. 7 the cross section of the cavity 16 is elliptical. These two variants are characterized by an especially high stability of the anchoring section, accompanied by low weight.

Figure 8:
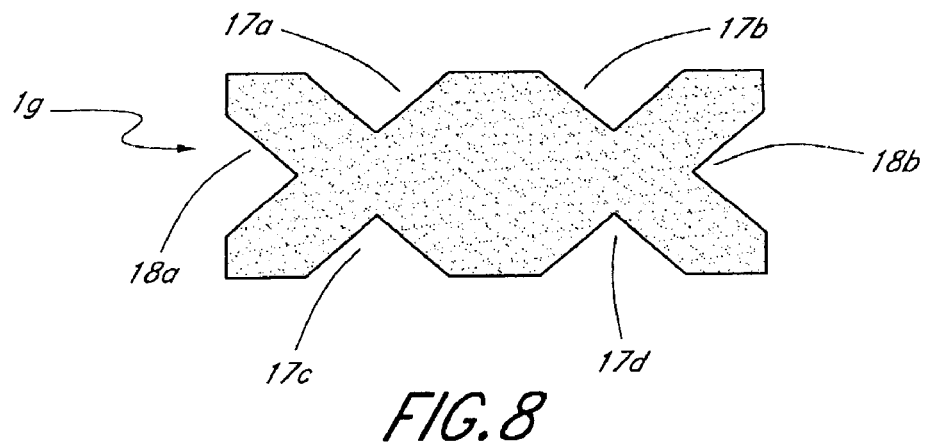

The variant according to FIG. 8 has an anchoring section 1g defined by a rectangular notched profile. On the anterior and on the posterior aspect there are formed two spaced-apart longitudinal notches 17a, 17b and 17c, 17d respectively. Each of these four notches is V-shaped. On the lateral and on the medial aspect one longitudinal notch 18a, 18b is provided, which likewise are V-shaped notches or longitudinal grooves. The corners that delimit the outline of the anchoring section 1g, like those in the embodiment according to FIGS. 6 and 7, can comprise flattened or concave facets like those shown in FIG. 5.

In the embodiment according to FIG. 6 the rectangular cavity 15 can be subdivided by a web or a cross-strut extending in the long direction of the shaft.

The embodiment according to FIG. 8, like that in FIG. 5, can be constructed as a hollow profile with a cavity that extends in the long direction of the shaft and has a circular or oval or elliptical cross section.

Figure 9:
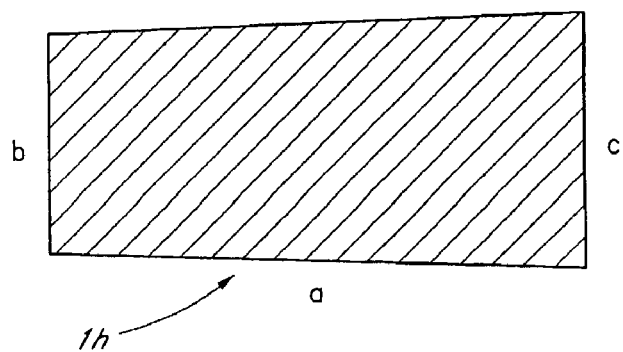

The embodiment of an anchoring section 1h shown in FIG. 9 differs from the embodiments in FIGS. 2-8 in having a trapezoidal cross section, which in this case is symmetrical with two equally long longer sides a in cross section, which correspond to the anterior and posterior surfaces, and two differently long shorter sides b, c, of which the shorter one is medial and the longer one lateral. This symmetrical trapezoidal shape is at present regarded as preferred, but in principle prosthesis shafts with asymmetrical trapezoidal cross sections can also be constructed.

The cross-sectional shapes shown in FIGS. 2-8 (which in those figures are, so to speak, inscribed within a rectangle) can also be modified to give them a basically trapezoidal shape: for instance, an asymmetrical oblique cross, an "H" with a longer and a shorter limb, an embodiment similar to that in FIG. 4 with three differently long limbs, an embodiment corresponding to FIG. 5 but with concave facets in the corner regions of a trapezoidal cross section, or various hollow profiles with a trapezoidal external configuration.

Figure 10:
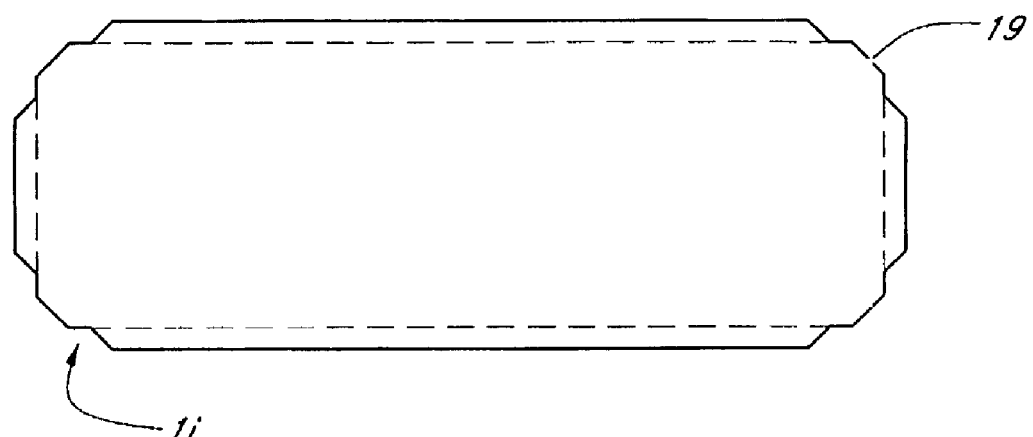
FIG. 10 shows another cross section of the anchoring section of the shaft in FIG. 1, in accordance with another embodiment.

In FIG. 10, to illustrate an additional special embodiment of the anchoring section of the shaft prosthesis in accordance with the invention, a cross-sectional shape is shown which again is basically rectangular and at all corners exhibits stepwise chamfered regions 19. The outer contour indicated by the dashed line approximately represents a conventional shaft cross section for the same application, with chamfered regions at an angle of 45° to the side surfaces. It is evident that the proposed new design (indicated by a continuous line) is over-dimensioned in comparison with this known embodiment over the greater part of all the side surfaces. However, all the chamfered regions have a middle section, the level of which coincides with the level of chamfering of the corresponding conventional prosthesis shaft. On either side of, and parallel to, this section are chamfered steps, set back slightly from the middle section.

This embodiment is based on the idea that it is advantageous for a prosthesis shaft—at least in its proximal region—to be over-dimensioned by a predetermined amount in comparison to the dimensions of the prepared cavity in the femur (i.e., in comparison to the "rasped dimension"), inasmuch as this over-dimensioning increases the pressure of the surfaces against the surrounding bone tissue and thus causes a degree of bone compression. In other words, one or both of a dimension between the medial and lateral surfaces and/or a dimension between the anterior and posterior surfaces is over-dimensioned with respect to the rasped dimension. When the ordinary forging precision is also taken into account, the over-dimensioning amounts to about 1-3% of the "rasped dimension" in the marrow space, which is also to be understood as the "null dimension".

In the corner regions (e.g. the diagonal dimensions), by contrast, the fit should be as precise as possible so as not to place the corticalis under excessive stress. Therefore the corner regions are reduced to the exact rasped dimension just prior to implantation. A final shaping to produce the stepped corner configuration shown in FIG. 10 has proved to be relatively easy to accomplish and advantageously effective; in principle, however, other fine structures in the corner region are possible, with which the dimensional conformity of the corners (more precisely the chamfers) can be made consistent with an over-dimensioning of the remaining side and end surfaces—for example, rounding or additional chamfered regions at an angle to the main chamfer.

All the characteristics disclosed in the application documents are claimed as essential to the invention insofar as they are new to the state of the art individually or in combination.

What is claimed is:

1. A method of implanting a hip-joint prosthesis in a femur, the method comprising:
   providing a shaft of a hip-joint prosthesis having a femur-anchoring section tapering along a longitudinal axis toward a distal end, said femur anchoring section further comprising an anterior face, a posterior face, a lateral face and a medial face with corner facets defined at junctions of adjacent faces, the shaft having an external contour with a substantially trapezoidal shape in a plane perpendicular to the longitudinal axis, the corner facets having a concave shape;
   rasping a cavity in an interior of a femur and shaping an anchoring section of the cavity to have an anterior-posterior dimension that is smaller than a corresponding anterior-posterior dimension of the shaft; and
   shaping the facets in the anchoring section of the shaft to match the rasped dimensions in corner regions of the cavity.

2. The method of claim 1, further comprising shaping the anchoring section of the cavity to have a medial-lateral dimension that is smaller than a corresponding medial-lateral dimension of the shaft.

3. The method of claim 2, further comprising shaping the medial-lateral dimension of the cavity to be 1 to 3% smaller than the corresponding medial-lateral dimension of the shaft.

4. The method of claim 1, further comprising shaping the anterior-posterior dimension of the cavity to be between about 1% to about 3% smaller than the corresponding anterior-posterior dimension of the shaft.

5. The method of claim 1, wherein shaping the facets is performed after rasping the cavity.

6. The method of claim 1, wherein the medial side of the shaft is shorter than the lateral side of the shaft.

7. The method of claim 6, wherein a length of the anterior and posterior sides of the shaft are substantially equal to one another.

8. A method for implanting a hip-joint prosthesis in a femur, the method comprising:
forming a longitudinal cavity in a femur with a rasp, the cavity having a proximal region and a distal region, the cavity having an anterior face, a posterior face generally opposite the anterior face, a lateral face, and a medial face generally opposite the lateral face, each of the faces disposed adjacent another of the faces and defining a junction therebetween;
reducing at least one pair of corners of a prosthetic femoral shaft to match the corresponding junctions of the rasped cavity, said at least one pair of corners being diagonally opposite each other as viewed in a cross-section of the shaft generally perpendicular to a longitudinal axis of the shaft; and
implanting the prosthetic femoral shaft in the cavity such that a distance between an anterior face and a posterior face of the shaft is over-dimensioned relative to a distance between the anterior and posterior faces of the cavity.

9. The method of claim 8, where in the distance between the anterior and posterior faces of the shaft in a proximal region of the shaft is over-dimensioned relative to the distance between the anterior and posterior faces of the cavity in the proximal region of the cavity.

10. The method of claim 8, wherein the distance between the anterior and posterior faces of the shaft is over-dimensioned relative to the distance between the anterior and posterior faces of the cavity by between about 1% and about 3%.

11. The method of claim 8, wherein a distance between diagonally opposite corners of the shaft is equal to a distance between diagonally opposite junctions in the cavity.

12. The method of claim 8, wherein a distance between a medial face and a lateral face of the shaft is over-dimensioned relative to a distance between the medial and the lateral faces of the cavity.

13. A method for implanting a hip-joint prosthesis in a femur, the method comprising:
rasping a cavity in a femur, the cavity having an anterior face, a posterior face generally opposite the anterior face, a lateral face, and a medial face generally opposite the lateral face, each of the faces disposed adjacent another of the faces and defining a junction therebetween;
providing a shaft of a hip-joint prosthesis having a femur-anchoring section tapering along a longitudinal axis toward a distal end, said femur anchoring section further comprising an anterior face, a posterior face, a lateral face and a medial face and having an external contour with a rectangular shape in a cross-section perpendicular to the longitudinal axis of the shaft;
shaping corner facets in the shaft, as viewed in a cross-section of the shaft generally perpendicular to a longitudinal axis of the shaft, at junctions between two of the anterior, posterior, lateral and medial faces of the shaft, wherein shaping the corner facets includes shaping the corner facets after rasping the cavity and prior to implantation of the shaft in the cavity; and
implanting the shaft within the cavity,
wherein the shaft is overdimensioned relative to the cavity only in the anterior-posterior direction of a proximal end of the shaft by between about 1-3%.

14. A method for implanting a hip-joint prosthesis in a femur, the method comprising:
rasping a cavity in a femur, the cavity having an anterior face, a posterior face generally opposite the anterior face, a lateral face, and a medial face generally opposite the lateral face, each of the faces disposed adjacent another of the faces and defining a junction therebetween;
providing a shaft of a hip-joint prosthesis having a femur-anchoring section tapering along a longitudinal axis toward a distal end, said femur anchoring section further comprising an anterior face, a posterior face, a lateral face and a medial face and having an external contour with a rectangular shape in a cross-section perpendicular to the longitudinal axis of the shaft;
shaping corner facets in the shaft, as viewed in a cross-section of the shaft generally perpendicular to a longitudinal axis of the shaft, at junctions between two of the anterior, posterior, lateral and medial faces of the shaft, wherein shaping the corner facets includes shaping the facets to have a concave shape; and
implanting the shaft within the cavity,
wherein the shaft is overdimensioned relative to the cavity only in the anterior-posterior direction of a proximal end of the shaft by between about 1-3%.

15. A method for implanting a hip-joint prosthesis in a femur, the method comprising:
rasping a cavity in a femur, the cavity having an anterior face, a posterior face generally opposite the anterior face, a lateral face, and a medial face generally opposite the lateral face, each of the faces disposed adjacent another of the faces and defining a junction therebetween;
providing a shaft of a hip-joint prosthesis having a femur-anchoring section tapering along a longitudinal axis toward a distal end, said femur anchoring section further comprising an anterior face, a posterior face, a lateral face and a medial face and having an external contour with a rectangular shape in a cross-section perpendicular to the longitudinal axis of the shaft;
shaping corner facets in the shaft, as viewed in a cross-section of the shaft generally perpendicular to a longitudinal axis of the shaft, at junctions between two of the anterior, posterior, lateral and medial faces of the shaft, wherein shaping the corner facets includes shaping the corner facets to match corresponding junctions in the rasped cavity so a dimension between diagonally opposite corner facets matches a dimension between corresponding diagonally opposite junctions in the rasped cavity; and
implanting the shaft within the cavity,
wherein the shaft is overdimensioned relative to the cavity only in the anterior-posterior direction of a proximal end of the shaft by between about 1-3%.

* * * * *

UNITED STATES PATENT AND TRADEMARK OFFICE
CERTIFICATE OF CORRECTION

PATENT NO. : 7,455,693 B2  
APPLICATION NO. : 11/432914  
DATED : November 25, 2008  
INVENTOR(S) : Karl Zweymuller It is certified that error appears in the above-identified patent and that said Letters Patent is hereby corrected as shown below:

On Col. 2, line 52, delete "1a" and insert --1i--, therefor.

Signed and Sealed this

Fourteenth Day of April, 2009

JOHN DOLL  
*Acting Director of the United States Patent and Trademark Office*